(12) United States Patent
Seligman

(10) Patent No.: US 6,890,314 B2
(45) Date of Patent: May 10, 2005

(54) KNEE BRACE HINGE DEFLECTOR

(75) Inventor: Scott Seligman, Carlsbad, CA (US)

(73) Assignee: DJ Orthopedics, LLC, Vista, CA (US)

( * ) Notice: Subject to any disclaimer, the term of this patent is extended or adjusted under 35 U.S.C. 154(b) by 207 days.

(21) Appl. No.: 09/945,377

(22) Filed: Aug. 31, 2001

(65) Prior Publication Data

US 2003/0060745 A1 Mar. 27, 2003

(51) Int. Cl.$^7$ ................................................ A61F 5/32
(52) U.S. Cl. ................................................ 602/26; 602/16
(58) Field of Search ............................ 602/5, 1, 23

(56) References Cited

U.S. PATENT DOCUMENTS

| | | | |
|---|---|---|---|
| 932,177 A | | 8/1909 | Roth |
| 2,195,024 A | | 3/1940 | Bullock |
| 2,632,440 A | * | 3/1953 | Hausser et al. ............... 602/16 |
| 2,959,168 A | * | 11/1960 | Shook .......................... 602/26 |
| 3,742,517 A | * | 7/1973 | Bednarczuk et al. .......... 602/16 |
| 3,902,482 A | * | 9/1975 | Taylor .......................... 602/16 |
| 4,524,764 A | * | 6/1985 | Miller et al. .................. 602/16 |
| 4,732,143 A | * | 3/1988 | Kausek et al. ................ 602/16 |
| 4,768,500 A | * | 9/1988 | Mason et al. ................. 602/26 |
| 4,777,941 A | * | 10/1988 | Borig et al. .................. 602/16 |
| 4,791,916 A | * | 12/1988 | Paez ............................. 602/26 |
| 4,966,133 A | * | 10/1990 | Kausek ......................... 602/16 |
| 5,000,170 A | * | 3/1991 | Young et al. .................. 602/16 |
| 5,005,565 A | * | 4/1991 | Fratesi ......................... 602/16 |
| 5,038,765 A | * | 8/1991 | Young et al. .................. 602/16 |
| 5,086,760 A | | 2/1992 | Neumann et al. |
| 5,092,320 A | * | 3/1992 | Maurer ......................... 602/26 |
| 5,288,287 A | | 2/1994 | Castillo et al. |
| 5,292,303 A | | 3/1994 | Bastyr et al. |
| 5,306,230 A | * | 4/1994 | Bodine ......................... 602/26 |
| 5,383,845 A | | 1/1995 | Nebolon |
| 5,409,449 A | | 4/1995 | Nebolon |
| 5,415,625 A | * | 5/1995 | Cassford et al. .............. 602/26 |
| 5,458,565 A | | 10/1995 | Tillinghast, III et al. |
| 5,472,412 A | * | 12/1995 | Knoth .......................... 602/26 |
| 5,527,268 A | | 6/1996 | Gildersleeve et al. |
| 5,674,188 A | * | 10/1997 | Young .......................... 602/26 |
| 5,693,007 A | * | 12/1997 | Townsend ..................... 602/26 |
| 5,807,294 A | * | 9/1998 | Cawley et al. ................ 602/26 |

FOREIGN PATENT DOCUMENTS

| EP | 0 884 035 A1 | * 12/1998 |
|---|---|---|
| WO | WO 00/74612 A1 | 12/2000 |
| WO | WO 01/10360 A1 | 12/2001 |

OTHER PUBLICATIONS

WO 01/10360 A1.*
Copy of Annex to Form PCT/ISA/206; communication relating to the results of the partial international search report.
*1988 Bracing Catalog*, DonJoy, A Member of the Smith and Newphew group, Carlsbad, CA.

* cited by examiner

Primary Examiner—Nicholas D. Lucchesi
Assistant Examiner—Huong Q. Pham
(74) *Attorney, Agent, or Firm*—Knobbe Martens Olson & Bear LLP

(57) ABSTRACT

A knee brace hinge deflector is provided for preventing interference and/or locking of the medial hinges of bilateral knee braces. The hinge deflector includes a shell having rounded surfaces for encasing a first medial hinge assembly and deflecting a second medial hinge assembly of bilaterally worn knee braces.

17 Claims, 3 Drawing Sheets

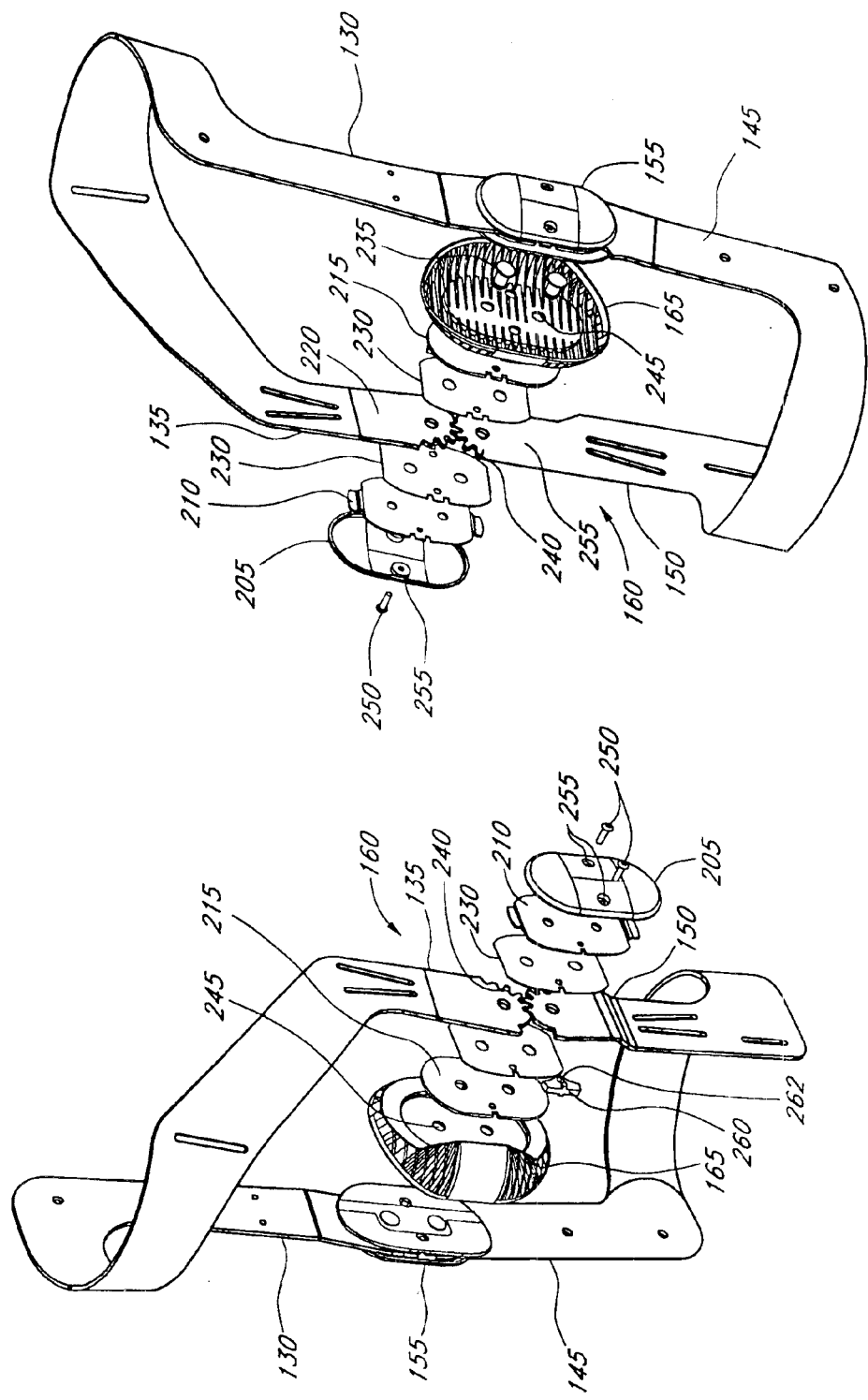

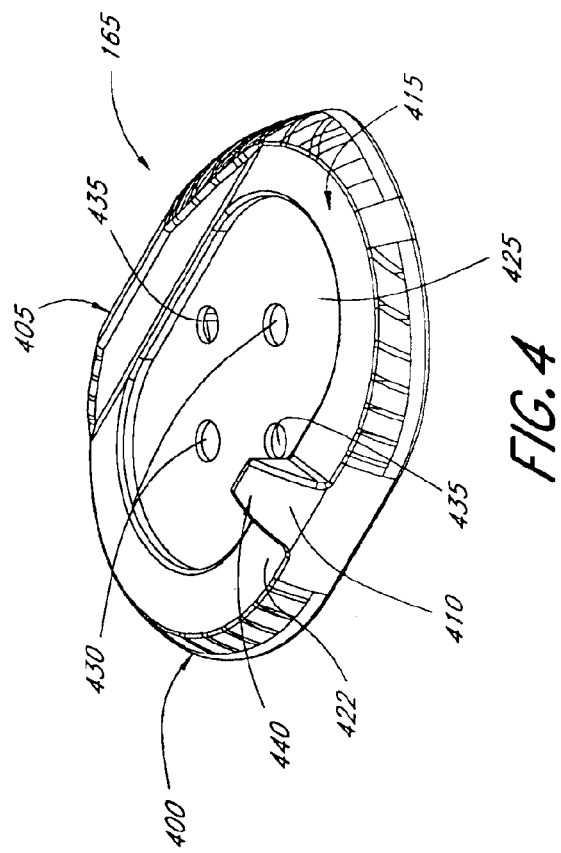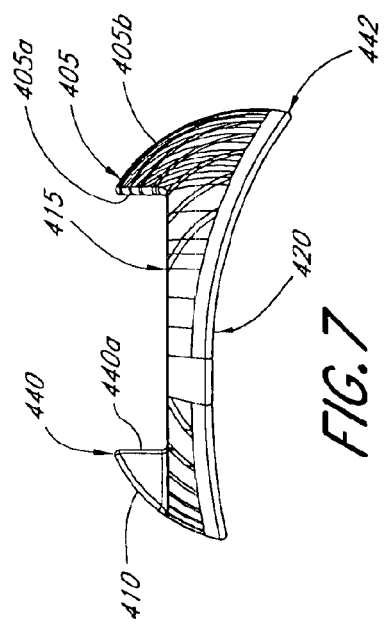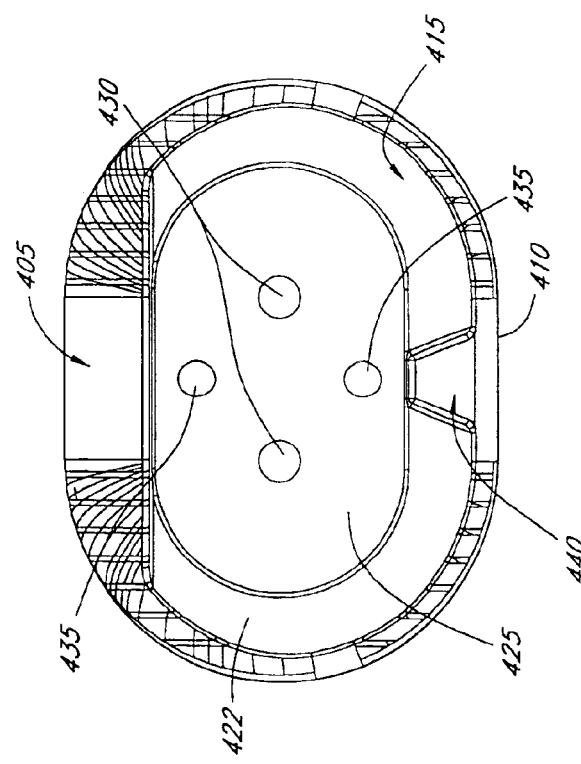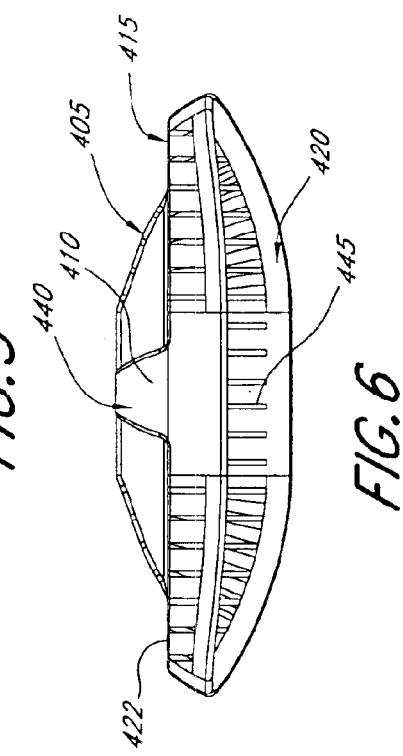

KNEE BRACE HINGE DEFLECTOR

BACKGROUND OF THE INVENTION

1. Field of the Invention

The present invention relates to medical devices and, in particular, to an improved knee brace hinge.

2. Description of the Related Art

Many types of braces have been made available for the support of body joints which have become weakened as a result of sports activity, accident, deterioration due to age, or disease. Braces for the knee are designed primarily to provide support while enabling the knee to function during normal activity.

Knee braces are often utilized by people who have suffered a knee injury and require some means of protection against further aggravation of the knee during rehabilitation. A knee brace can limit the amount of damage to an injured knee by providing the patient with adequate knee stabilization and control. Stabilization and control is achieved in such a manner as to permit the patient relative freedom in the normal use of the knee joint while, at the same time, permitting control over the joint so as to optimize healing.

In addition, knee braces are often employed by a person having previously suffered a knee injury who wishes to actively participate in strenuous and demanding physical activity. In such cases where the person seeks knee support in furtherance of activities involving heavy running or sprinting, it is extremely advantageous to design a knee brace which most accurately simulates the true motions of the anatomical knee joint. This will minimize the leg forces required to overcome mismatched motions and generally increase comfort levels.

Knee braces generally serve two purposes. Firstly, the brace has to support the knee at all times, but especially during movement. Secondly, the brace should limit knee movements in flexion or extension within limits beyond which injury to the knee may occur. Further, movements are confined to the varus/valgus plane.

Flexion is defined as flexing of the knee from the extended position to a position where the foot and ankle is bent towards the thigh. Extension is defined as being the opposite movement. An extended leg is normally straight with virtually no bending at the knee joint.

Knee braces for providing support for the knee of a person are well known in the art. Such braces generally include a tibial shell which is constructed so as to be closely configured to the shape of the lower leg and a femoral shell which is constructed so as to be closely configured to the shape of the thigh area of the leg. The two shells are secured to their respective areas on the leg and are interconnected by some type of mechanism so as to pivot relative to each other as the knee is bent. The mechanism is usually a pair of hinge joints, one on each side of the knee brace, with the tibial shell usually being attached to the lower part of each one of the two knee joints and the femoral shell usually being attached to the upper part of each one of the two hinge joints.

Often, a person will wear knee braces bilaterally. When wearing double upright rigid knee braces bilaterally, the medial hinges often interfere with one another. The hinges sometimes lock together, causing the knee brace wearer to fall or injure himself. This problem is evident during normal walking and running, but becomes pronounced in activities such as snow skiing or motocross.

Therefore, there is a need for an improved knee brace which prevents interference and/or locking between the medial hinges.

SUMMARY OF THE INVENTION

The present invention provides an improved knee brace including an upper portion and a lower portion pivotally attached at a hinge, which permits rotation of the upper portion with respect to the lower portion. A plurality of adjustable straps secures the knee brace to the leg. A hinge deflector encases the hinge and prevents locking of opposite medial hinges during bilateral knee brace use.

The hinge assembly includes a hinge cover, parallel plates and a plurality of fasteners for connecting the plates, cover, and hinge deflector to the knee brace. The hinge deflector comprises a shell having rounded surfaces, which encase the internal components of the medial hinge and also deflects the opposing medial hinge.

BRIEF DESCRIPTION OF THE DRAWINGS

FIG. 2 is a perspective exploded view of a knee brace hinge of the knee brace of FIG. 1.

FIG. 3 is a perspective exploded view of a knee brace hinge of the knee brace of FIG. 1.

FIG. 4 is a perspective view of a knee brace hinge deflector of the knee brace of FIG. 1.

FIG. 5 is a top view of the knee brace hinge deflector of FIG. 4.

FIG. 6 is a side view of the knee brace hinge deflector of FIG. 4.

FIG. 7 is an end view of the knee brace hinge deflector of FIG. 4.

DETAILED DESCRIPTION OF THE PREFERRED EMBODIMENTS

Knee Brace

Figure 1:
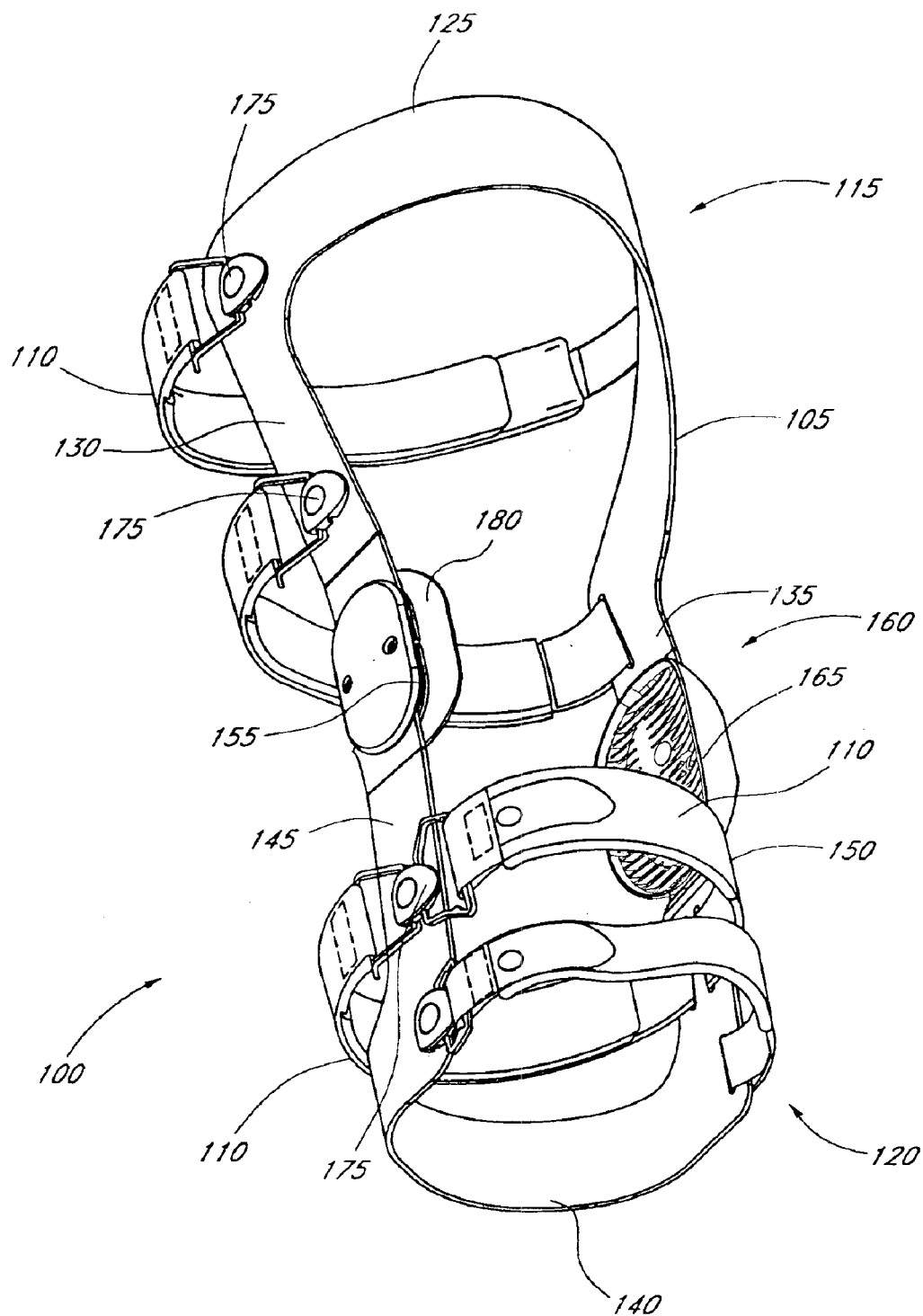
FIG. 1 is a perspective view of a knee brace of the present invention.

FIG. 1 shows an orthopedic brace for supporting a joint having a plurality of compliant support components. The knee brace 100 of the present invention includes a hinged shell 105 and a plurality of adjustable support straps 110 engaging the brace at two points on opposite sides of the hinge to stabilize the weakened joint throughout its range of motion. The shell 105 has an upper portion 115 conformable to the thigh and a lower portion 120 conformable to the lower leg. Each of the shell portions 115, 120 is preferably formed from a single continuous shaped piece of a stiff material such as certain plastics, fiberglass, composites, certain metals, and the like, as are known to those of skill in the art.

The upper portion 115 includes a cuff 125, having a lateral arm 130 and a medial arm 135. The cuff 125 has a preformed arcuate shape sized to snugly conformingly engage the anterior portion of the thigh.

The lower portion 120 includes a cuff 140, having a lateral arm 145 and a medial arm 150 extending therefrom. The lower portion 120 has substantially the same structure as the upper portion, but is sized to conform to the lower leg of the user. The lower cuff 140 has substantially the same configuration as the upper cuff 125, but the preformed arcuate shape thereof is sized somewhat smaller to snugly conformingly engage the calf of the lower leg.

The upper and lower portions 115, 120 are connected across rotatable hinges 155, 160. More specifically, lateral upper arm 130 is pivotally connected to lateral lower arm 145 and medial upper arm 135 is pivotally connected to medial lower arm 150 across lateral hinge 155 and medial hinge 160, respectively. A resilient pad 180 may also be provided to cushion the knee joint from the rigid hinges 155, 160. (For simplicity, a pad is only shown on the hinge 155.)

Medial hinge 160 also preferably includes a hinge deflector 165 for preventing interference between medial hinges when a user is wearing a knee brace on each leg. The hinge deflector 165 acts as a shield to the internal components of the medial hinge 160 and deflects the opposite medial hinge, preventing the hinges from locking together.

The support straps 110 are preferably adjustable in length, enabling the user to modify the support strap tension, and consequently the degree of support the brace provides to the joint. Support straps 110 are preferably formed from a wear-resistant supple material such as pliant leather, or natural or synthetic cloth, such as nylon and the like. The material should be compliant, but substantially unstretchable.

Support straps 110 enable closure of brace 100 around the limb on which the brace is mounted. As seen in FIG. 1, each of the cuffs 125, 140 is held in place by straps, and a strap connector. A separate strap is provided at the upper arms, surrounding the upper leg. A separate strap is provided at the lower arms, surrounding the lower leg. Each strap is integrally provided with a tab and cap fastener assembly 175 at the ends thereof to fix the strap and enable adjustment to the length of the straps 110 for close conformance of the shell 105 to the limb on which the brace is mounted.

Hinge Assembly

Referring to FIGS. 2 and 3, an exploded medial hinge assembly 160 and hinge deflector 165 are shown. Lateral hinge assembly 155 is also shown. It will be apparent to one of skill in the art that the hinge assembly 160 and an associated hinge deflector 165 can be incorporated into many other types of conventional hinged orthopedic braces without substantial modification. It is also appreciated that lateral hinge assembly 155 has the same features as medial hinge assembly 160. Although hinge deflector 165 is intended for use with medial hinge assembly 160, it is appreciated that hinge deflector 165 may also be used with lateral hinge assembly 155.

The hinge assembly 155, 160 comprises a hinge cover 205, parallel plates 210, 215, an upper rotary connector 220 and a lower rotary connector 225. Washers 230 may also be provided between parallel plates 210, 215 and connectors 220, 225. The cover 205 and plates 210, 215 are formed from one or more high-strength, rigid materials, such as metals or plastics. Upper and lower rotary connectors 220, 225 are respectively formed integrally with the upper and lower cuff arms 130, 135 and 145, 150. The connectors 220, 225 have semi-circular ends that are pivotally anchored by rivets 235 and are provided with interlocking teeth 240. This construction of the hinge assembly 155, 160 enables rotatable engagement of the upper and lower rotary connectors 220, 225 and correspondingly enables rotation of the upper and lower portions 115, 120 relative to each other.

The hinge deflector 165 is secured to the parallel plates 210, 215, and connectors 220, 225 by rivets 235, or other suitable fasteners, passing through apertures 245. Hinge cover 205 is secured to the parallel plates 210, 215 and connectors 220, 225 by screws 250, or other suitable fasteners, passing through apertures 255.

A hinge extension stop 260 is preferably provided to interface with rotary connectors 220, 225 at interlocking teeth 240. Extension stop 260 limits the range of motion of the rotary connectors 220, 225 and, consequently, brace 100.

Hinge Deflector

The hinge deflector 165 shown in detail in FIGS. 4–7 comprises a thin walled shell 400 which is configured to encase the hinge assembly. The shell 400 has a generally elliptical shape as viewed in FIGS. 4 and 5. The shell has an outer or hinge side 415 which faces the hinge, encasing the hinge assembly, and facing away from the knee. The shell also has an inner side 420 which faces the knee, and thus may be referred to as the knee side. As seen in FIGS. 2 and 3, the shell is actually positioned between the knee and the brace hinge, although shell portions extend to the outer side of the hinge.

The shell outer side 415 includes an outer perimeter surface 422 surrounding a central recess 425 having a generally elliptical shape also. The plate 215 and washer 230 of the hinge assembly fit within the recess 425.

The bottom wall of the recess includes a plurality of apertures 430 for attaching the hinge assembly to the knee brace. Two apertures 430 are shown, lying approximately on a longitudinal axis of the recess for attaching the hinge deflector to the knee brace with the fasteners or rivets 235 which pass through the components of the hinge assembly and the knee brace. Two apertures 435 are also shown, lying on an axis generally perpendicular to the longitudinal axis, for securing the plates 210 and 215 with the screws or fasteners 250. One of the fasteners passes through a hole 262 in the stop 260 for securing the stop 260 between the plates 210 and 215.

The outer side 415 includes a projection 405 which extends along a majority of the length of one side of the elliptically-shaped shell 400. This can be referred to as the forward side or edge in that it is the side closest to the forward portion of a person's knee when the brace is in use. The projection includes a straight inner wall 405*a* which protrudes from the recess 425 and the surrounding surface 422, with a portion of that wall being flush with one side of the wall of the recess. The projection includes an outer surface 405*b* which slopes toward a peripheral skirt 442, and an outer edge of the shell 400, as seen in FIG. 7. While the central portion of the projection curves basically toward the edge, as seen in FIG. 7, the projection ends taper or curve to the surface 422, as seen in FIGS. 4 and 6.

The outer side 415 also includes a projection 440 extending from surface 422 on the edge of the shell opposite from the projection 405. That edge of the shell can be referred to as the rear edge since it is closest to the back of the knee when the brace is in use. As seen, the projection 440 is only in the central portion of that edge as is needed for the rotational movement of the hinge. The projection 440 limits this movement. The projection 440 also has a straight inner wall 440*a* and an outer curved surface 410, for deflecting external objects. The curved surfaces 405*b* and 410 curve inward toward the knee brace and hinge assembly when assembled, for deflecting an interfering external object. The curved surfaces 405*b* and 410 have approximately the same slope; however, different slopes may be employed and the curved surface 405*b* preferably extends further than the curved surface 410. The outer skirt 442 of the outer side 415 is also slightly tapered, so that there are no edges for interfering with the hinge. As seen, both projections extend above the surface 422 about the same amount to perform their deflector function.

The shell inner side 420 preferably includes a plurality of ribs 445 for providing additional strength to the hinge deflector.

In a preferred embodiment, hinge deflector 165 is a molded plastic material. However, any material having sufficient rigidity to withstand impact forces encountered during impact of hinge assemblies during physical activities are contemplated herein.

Resilient pad similar to the pad 180 shown on hinge 155 in FIG. 15 is preferably releasably fastened to the shell inner side 420 by conventional releasable fastening means such as a hook and hoop fastener coupling, commonly referred to as VELCRO, wherein one element of the coupling is substantially permanently affixed to the inner side 420 and the other element of the coupling is substantially permanently affixed to resilient pad 180. The resilient pad may be any knee brace pad, as known to those of skill in the art.

Referring to FIGS. 2 and 3 as well as the description of the deflector shell, it may be seen that the deflector is positioned on the knee or inner side of the knee brace hinge. The plate 210 and washer 230 fit into the recess in the hinge side of the shell. The hinge side is next placed against the rotary hinge connectors 220 and 225, with the connectors fitting between the projections 405 and 440. A washer 230 and the plate 215 covered by the hinge cover 205 are next positioned adjacent the connectors and between the projections 405 and 440. The upper edges of the projections are about flush with the outer surface of the hinge cover 205 so that interference of that cover with adjacent objects is deflected by the curved surfaces 405b and 410. Thus, it can be seen that an entire hinge assembly is substantially encased by the deflector shell.

The hinge deflector prevents locking and/or interference of a medial hinge of another knee brace or, alternatively, prevents locking with other external devices, such as components of a motocross bike. The hinge deflector 165 encases the hinge and deflects the external object with curved surfaces 405b, 410. The curved surfaces 405b, 410 of the hinge deflector 165 prevent the locking because the external object slides along and off the curved surfaces 405b, 410. The protruding curved surfaces 405b, 410 extend out and over knee brace and hinge assembly to deflect any surfaces or objects that may interfere with knee brace function.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A knee brace, comprising:
   an upper portion;
   a lower portion;
   a plurality of straps for securing said upper portion to a person's thigh and said lower portion to a person's calf;
   medial and lateral hinges for pivotally coupling said upper and lower portions together; and
   a hinge deflector adapted to be worn between the person's knee and said medial hinge, said hinge deflector having an inner side adapted for facing the knee and an outer side opposite from the inner side and facing said medial hinge, said outer side being formed with a first projection extending around a front edge of said medial hinge, said projection having a curved surface along a front edge of said hinge deflector, said curved surface sloping in a rearward direction from said inner side of said hinge deflector toward an outer side of said medial hinge for deflecting an object away from said medial hinge.

2. The brace of claim 1, wherein said outer side of said hinge deflector is formed with a recess shaped for receiving at least a portion of said medial hinge.

3. The brace of claim 1, wherein said outer side of said hinge deflector further comprises a second projection extending away from the knee and around a rear edge of said medial hinge.

4. The brace of claim 3, wherein said second projection is positioned for contacting said upper and lower portions of the knee brace for limiting rotational movement of said medial hinge during flexion of the person's knee.

5. The brace of claim 1, wherein said hinge deflector is made of a molded plastic material.

6. The deflector of claim 1, further comprising a plurality of ribs along said inner side of said hinge deflector for increasing the structural integrity of said hinge deflector.

7. A medial hinge deflector having a shell configured to be positioned between a person's knee and a medial hinge of a knee brace, said shell having an inner side shaped for facing a medial portion of the person's knee and an outer side opposite from said inner side and facing said medial hinge, said outer side including a first projection extending around a front edge of the medial hinge, said first projection being formed with a curved surface sloping in a rearward direction from said inner side of said shell toward an outer side of said medial hinge, for deflecting an object away from the medial hinge.

8. The deflector of claim 7, wherein said outer side of said shell further comprises a recess shaped for receiving a portion of the medial hinge.

9. The deflector of claim 7, wherein said shell includes a plurality of openings for receiving fasteners to connect said shell to the knee brace.

10. The deflector of claim 7, wherein said shell is made of a molded plastic material.

11. The deflector of claim 7, wherein said outer side further comprises a second projection adapted to extend around a rear edge of the medial hinge, said second projection having a curved deflecting surface and being positioned to limit a range of motion of the medial hinge.

12. The deflector of claim 7, further comprising a plurality of ribs along said inner side for increasing the structural integrity of said shell.

13. The deflector of claim 7, wherein said shell has a substantially elliptical shape.

14. The deflector of claim 8, wherein said recess has a substantially elliptical shape.

15. A knee brace, comprising:
   an upper portion;
   a lower portion;
   a plurality of straps for securing said upper portion to a person's thigh and said lower portion to a person's calf;
   medial and lateral hinges for pivotally coupling said upper and lower portions together; and
   a hinge deflector adapted to be worn between the person's knee and said medial hinge, said hinge deflector having a contoured inner side configured for facing a medial portion of the person's knee and an outer side opposite from said inner side facing said medial hinge, said outer side being formed with a recess for receiving at least a portion of said medial hinge and including a first projection extending around a front edge of said medial hinge, said projection having a curved surface sloping in a rearward direction from said inner side of said hinge deflector toward an outer side of said medial hinge for deflecting an object away from said medial hinge.

16. The brace of claim 15, wherein said outer side of said hinge deflector further comprises a second projection extending away from the knee and around a rear edge of said medial hinge, said second projection being positioned for contacting said upper and lower portions of the knee brace for limiting rotational movement of said medial hinge during flexion of the person's knee.

17. The brace of claim 16, wherein said hinge deflector is made of a molded plastic material.

* * * * *

UNITED STATES PATENT AND TRADEMARK OFFICE
CERTIFICATE OF CORRECTION

PATENT NO. : 6,890,314 B2 Page 1 of 1
APPLICATION NO. : 09/945377
DATED : May 10, 2005
INVENTOR(S) : Scott Seligman It is certified that error appears in the above-identified patent and that said Letters Patent is hereby corrected as shown below:

At column 5, line 62, in Claim 1, after "from," delete "the" and insert --said--;

At column 6, line 20, in Claim 7, after "hinge," insert --comprising a hinge--;

At column 6, line 29, in Claim 7, before "for," delete ","; and

At column 6, line 63, in Claim 15, after "side," insert --and--.

Signed and Sealed this

Eighth Day of July, 2008

JON W. DUDAS
*Director of the United States Patent and Trademark Office*